United States Patent
Mankovich et al.

(10) Patent No.: US 9,600,882 B2
(45) Date of Patent: Mar. 21, 2017

(54) MULTI-STUDY MEDICAL IMAGE NAVIGATION

(71) Applicant: KONINKLIJKE PHILIPS N.V., Eindhoven (NL)

(72) Inventors: Gabriel Ryan Mankovich, Yorktown Heights, NY (US); Yuechen Qian, Briarcliff Manor, NY (US); Thusitha Dananjaya De Silva Mabotuwana, Yonkers, NY (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/430,927

(22) PCT Filed: Oct. 1, 2013

(86) PCT No.: PCT/IB2013/059027
§ 371 (c)(1),
(2) Date: Mar. 25, 2015

(87) PCT Pub. No.: WO2014/053986
PCT Pub. Date: Apr. 10, 2014

(65) Prior Publication Data
US 2015/0235365 A1    Aug. 20, 2015

Related U.S. Application Data

(60) Provisional application No. 61/708,160, filed on Oct. 1, 2012.

(51) Int. Cl.
G06K 9/00    (2006.01)
G06T 7/00    (2006.01)

(52) U.S. Cl.
CPC .. *G06T 7/0014* (2013.01); *G06T 2207/10004* (2013.01); *G06T 2207/10072* (2013.01); *G06T 2207/30004* (2013.01)

(58) Field of Classification Search
None
See application file for complete search history.

(56) References Cited

U.S. PATENT DOCUMENTS 6,711,590 B1 *  3/2004  Lennon ............... G06F 17/3079
8,934,695 B2 *  1/2015  Sato ...................... G06Q 10/10
                                                        382/131

(Continued)

OTHER PUBLICATIONS

"Chapter 8: Annotating and Measuring Images", eFilm Workstation 3.2 User's Guide (2009) pp. 137-149, p. 144, section Copying annotations and measurements, Mississauga, ON, Canada.

*Primary Examiner* — Amir Alavi

(57) ABSTRACT

A medical image navigation system (2) includes a viewport module (4), a proximity module (26), a visualization module (28) and a matching module (34). The viewport module (4) navigates a plurality of image slices of a study and based on input from at least one input device selects at least one image which is displayed and any annotations associated with the selected at least one image on a display device. The proximity module (26) for the selected image slice returns at least one proximate annotation, if available. The visualization module (28) for the returned at least one proximate annotation visualizes the at least one proximate annotation which is displayed by the viewport module on the selected at least one image. A matching module (34) retrieves for display an image slice in one study which corresponds to a displayed image slice from another study.

20 Claims, 7 Drawing Sheets

(56) References Cited

U.S. PATENT DOCUMENTS

| | | | |
|---|---|---|---|
| 2006/0215888 A1 | 9/2006 | Habets et al. | |
| 2009/0080744 A1* | 3/2009 | Sagawa | G06F 19/321 382/131 |
| 2009/0080752 A1 | 3/2009 | Ruth et al. | |
| 2009/0087067 A1* | 4/2009 | Khorasani | A61B 6/025 382/132 |
| 2009/0232378 A1* | 9/2009 | Nakamura | G06T 7/003 382/131 |
| 2011/0238618 A1* | 9/2011 | Valdiserri | G06F 19/321 707/608 |
| 2013/0187911 A1 | 7/2013 | Dries et al. | |
| 2013/0205247 A1 | 8/2013 | Erhard et al. | |
| 2014/0089000 A1* | 3/2014 | Takata | G06F 19/321 705/2 |
| 2014/0149407 A1* | 5/2014 | Qian | G06F 19/321 707/737 |
| 2015/0205917 A1* | 7/2015 | Mabotuwana | G06F 19/321 382/128 |

* cited by examiner

MULTI-STUDY MEDICAL IMAGE NAVIGATION

CROSS-REFERENCE TO PRIOR APPLICATIONS

This application is the U.S. National Phase application under 35 U.S.C. §371 of International Application No. PCT/IB2013/059027, filed on Oct. 1, 2013, which claims the benefit of U.S. Provisional Application No. 61/708,160, filed on Oct. 1, 2012. These applications are hereby incorporated by reference herein.

The following relates generally to medical imaging. It finds particular application in conjunction with navigation of diagnostic images and annotations within and between studies, and will be described with particular reference thereto. However, it will be understood that it also finds application in other usage scenarios and is not necessarily limited to the aforementioned application.

A radiologist or healthcare practitioner reviews images and/or image slices in a patient study on a monitor. A patient study may include a series of parallel slices spanning a region of the patient, e.g., 20-50 cm or more. The thickness of the slice varies with the imaging modality and is typically 1-5 mm. The healthcare practitioner uses a scroll bar or the like to step from image to image. When scrolling quickly the display has a cine type appearance. The healthcare practitioner makes annotations on various images and includes details in the annotations such as lesion measurements. A patient with multiple lesions typically has each lesion annotated, which can be spatially spread over a volume with many non-annotated images in between. The healthcare practitioner typically selects a few representative images and indicates the selected images as key images. Over time, a patient can have many studies. The healthcare practitioner compares images from the various studies to analyze the change in lesions and other tissues.

In order to compare images, the healthcare practitioner typically has the current study open on one monitor and opens a second or prior study on another monitor to compare. Each study contains a plurality of images from several hundred to several thousand images or slices. Images are ordered sequentially through each volume. The healthcare practitioner must verify when selecting a prior study that study is comparable with the current study. For example, the images are typically stored as DICOM images. The metadata of DICOM images includes a modality, the body part, protocol and other information. To make a comparison, the study information is reviewed for comparability by modality and body part. The patient may have had multiple studies for different conditions and/or anatomical regions such as an arm, leg, whole body, head, etc. The various studies can include many modalities such as magnetic resonance (MR), X-ray computed tomography (CT), Positron Emission Tomography (PET), and the like.

After finding a comparable study, the healthcare practitioner selects an image in the current study and/or a key image in a prior study, and to find a comparable image, the healthcare practitioner typically must scroll through images in the other study which consumes valuable clinical time. Furthermore, as the healthcare practitioner rapidly moves through the images, annotations can flash by so quickly that they are easily missed. With multiple prior studies, multiple annotations per study, spatial separation within a study, and longitudinal comparisons, considerable clinical time can be consumed simply scrolling through images and the possibility of missing appropriate prior annotations is highly possible.

In a longitudinal comparison, images are compared between many studies. To compare images, the healthcare practitioner opens each study, usually in comparison with the current study and finds the images from the same volume in each study and notes the included annotations. In order to find the images from the same volume in each study, the healthcare practitioner opens each study and scrolls through the images. The time performing the navigation often means a healthcare practitioner is consumed finding a comparable image and may spend less time comparing the images. Because of the difficulty in finding comparable images, meaningful relationships which can be revealed by moving between comparable images may be lost.

Annotations are related to an image or slice. Annotations appear as a slice or image is displayed. When scrolling through hundreds or thousands of images the time during which an image or slice is displayed and the corresponding annotations displayed can be a fraction of a second. No warning is given when an image with annotations is about to be displayed and no notice is given when an image with annotations has been displayed. The method relies on the visual perceptions of the healthcare practitioner and the healthcare practitioner to intuitively know where to look for annotations and to move slowly through the images when an annotation is likely to be found.

When annotating images, the goal of the radiologist or healthcare practitioner is to annotate an image slice with a best example of a finding. For example, in a lesion, the best example can include an image slice with the most well defined border to the lesion, or an image slice which shows a maximum dimension of the lesion. Once an annotation is made and a better example image slice is later found, the process of adding the annotation to the new image slice and deleting the annotation for the prior image slice can be a time consuming process.

The following discloses a new and improved multi-study image navigation which addresses the above referenced issues, and others.

In accordance with one aspect, a medical image navigation system includes a viewport module, a proximity module, and a visualization module. The viewport module navigates a plurality of image slices of a study and based on input from at least one input device selects at least one image which is displayed and any annotations associated with the selected at least one image on a display device. The proximity module for the selected image slice returns at least one proximate annotation. The visualization module for the returned at least one proximate annotation visualizes the at least one proximate annotation which is displayed by the viewport module on the selected at least one image.

In accordance with another aspect, a method of navigating medical images includes identifying at least one annotation associated with an image slice within a defined number of adjacent image slices of a plurality of image slices to a selected image slice. The identified annotations are visualized. The selected image and visualized annotations are displayed on a display device.

In accordance with another aspect, a medical image navigation system includes a viewport module, a context extraction module, and a matching module. The viewport module navigates a plurality of image slices of a current study and at least one prior study which includes a plurality of images and at least one key image, and based on input from at least one input device selects at least one key image, which is displayed on a display device with an associated image slice in the current study. The context extraction module extracts and associates contextual information with the at least one key image and the current study, and the contextual information includes a modality and a body part. The matching module compares the contextual information to determine if the studies are comparable, and then returns a location of an image slice in the current study associated to the selected at least one key image of the at least one prior study.

One advantage is image comparison between patient studies is facilitated.

Another advantage resides in expediting finding the location of annotations.

Another advantage resides in facilitating the annotation of images.

Another advantage resides in integration with existing image studies.

Another advantage resides in the integration with existing methods and systems.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of the medical image navigation system.

FIG. 2 diagrammatically illustrates an embodiment of multi-study image navigation.

Figure 6:
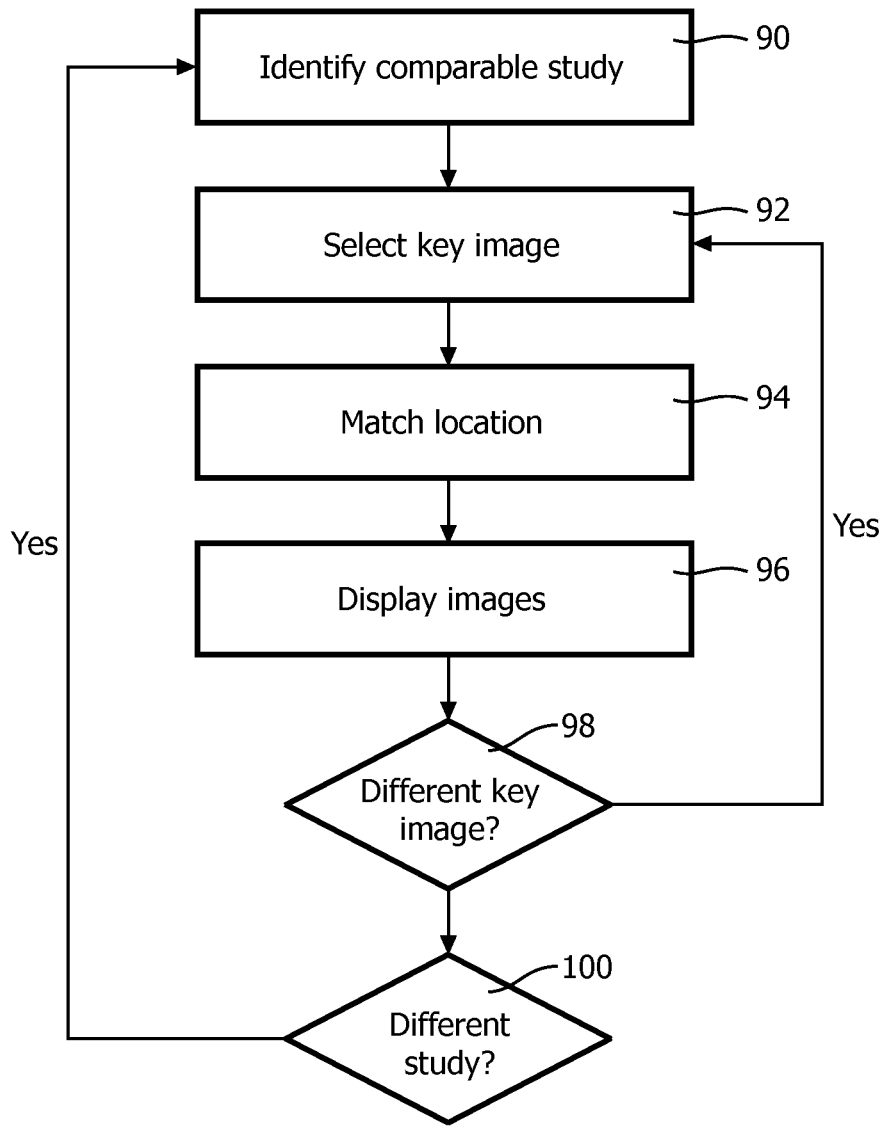

FIG. 6 flowcharts one method of multi-study image navigation.

Figure 7:
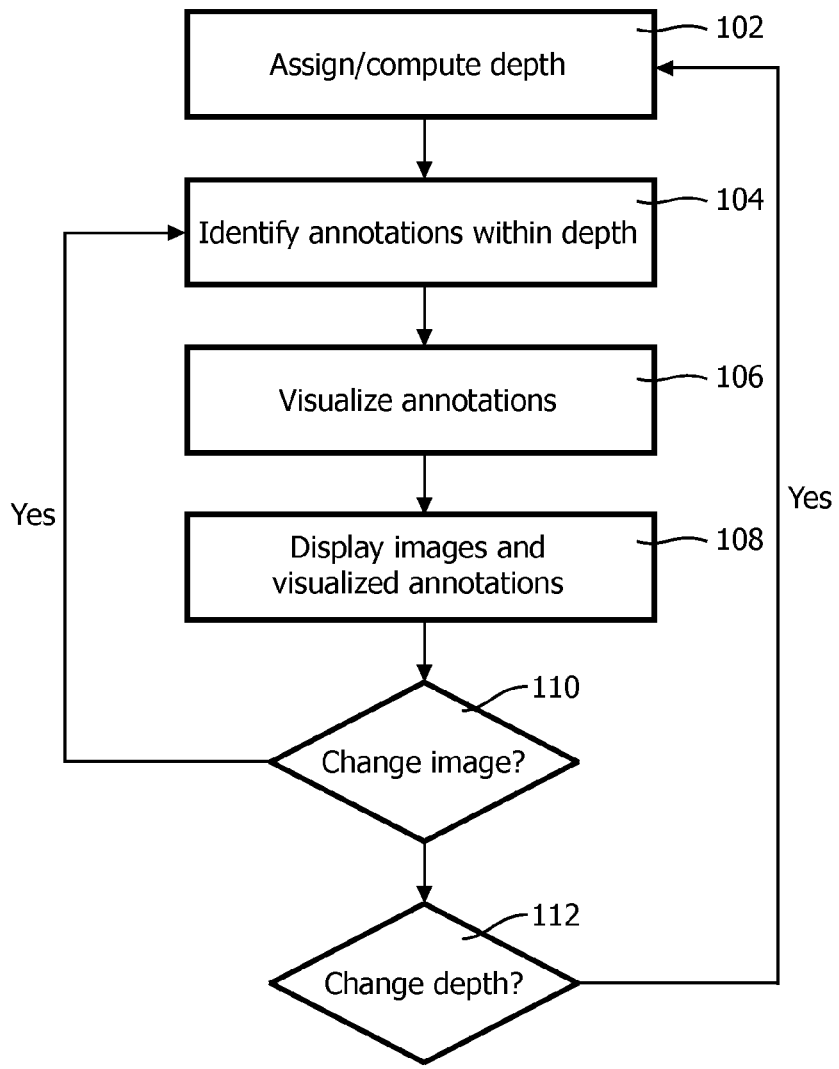

FIG. 7 flowcharts one method of visualizing proximate annotations.

Figure 8:
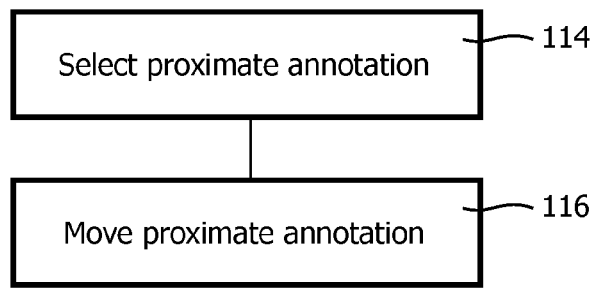

FIG. 8 flowcharts one method of editing proximate annotations.

Figure 1:
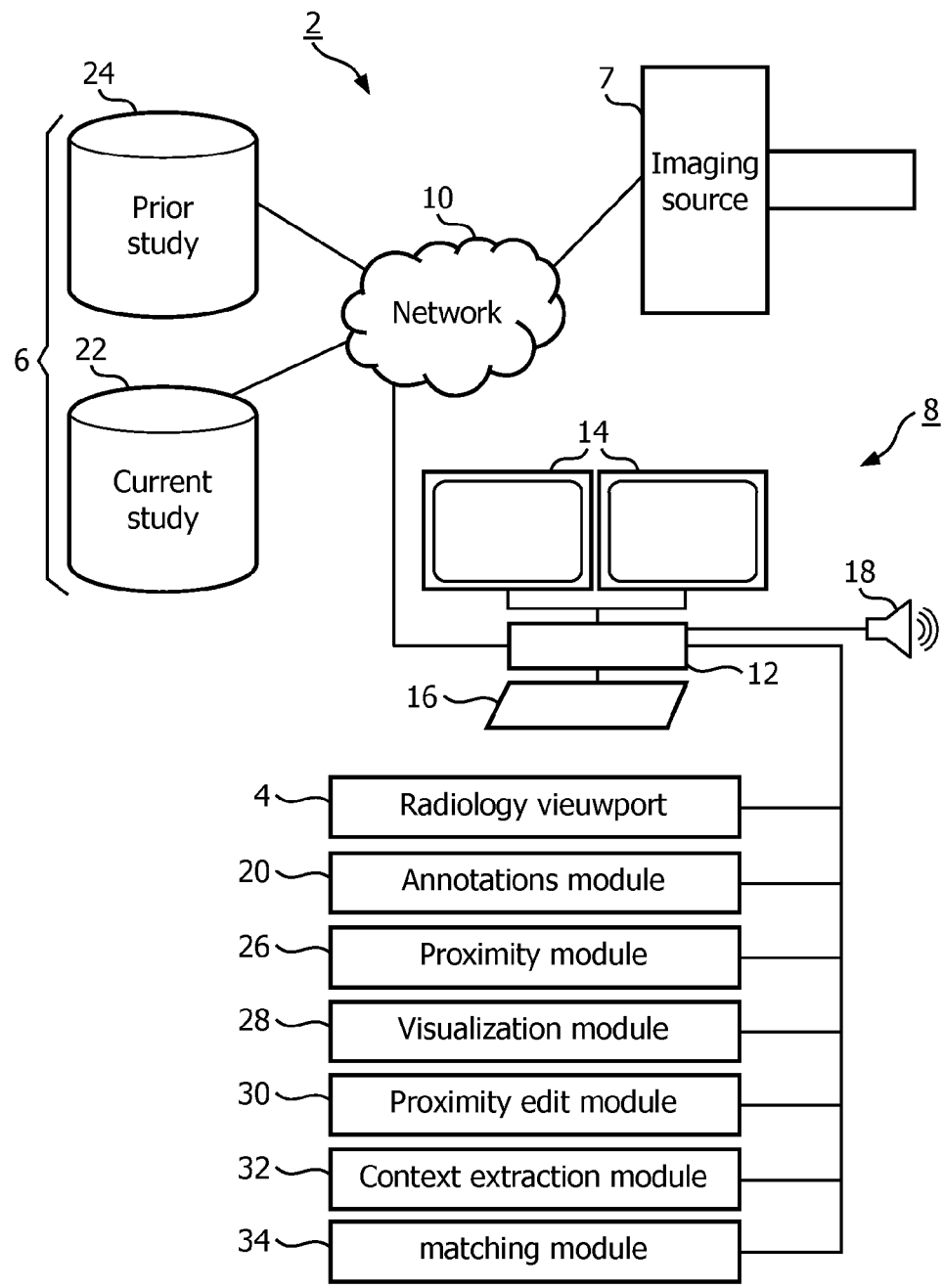

With reference to FIG. 1, an embodiment of the medical image navigation system 2 is schematically illustrated. The system 2 includes a radiology viewport module 4 which manages the user interface, opens and closes image studies, manages the displays, the input commands, and the like. The radiology viewport module opens image studies and each image study can include a plurality of images or image slices. The images are stored in a standard image format such as the Digital Imaging and Communications in Medicine (DICOM) format and in a memory or computer storage system 6 such as a Picture Archiving and Communication System (PACS), a Radiology Information System (RIS), and the like. The images can be retrieved from storage or received directly from an imaging source 7 such as an MR scanner, CT scanner, PET scanner, and the like.

The radiology viewport 4 operates on a workstation 8, a workstation connected via a network 10 to a server or webserver, and the like. The workstation 8 includes an electronic processor or electronic processing device 12, one or more displays 14 which displays the images and annotations, menus, panels, and user controls, the at least one input device 16 which inputs the healthcare practitioner selections, and optionally a speaker 18 for audible indicators and/or voice feedback. The workstation 8 can be a desktop computer, a laptop, a tablet, a mobile computing device, a smartphone, and the like. The input device can be a keyboard, a mouse, a microphone, and the like.

The system 2 includes an annotations module 20 which creates, stores, and associates one or more annotations with an image slice of a current study 22. Annotations can include multi-media formats such as text, graphics, voice, etc. Annotations can be displayed as representations such as geometric objects, freehand drawings, measurement lines, text boxes, etc., overlaying the image slices, or separate from the associated image such as a sidebar, palate, icons, etc. The annotations can be visual and/or audible. The annotations including the size, location, orientation, etc. are stored with the associated image. The annotations and associated image can be stored as pieces of an object, package, etc., or separately and dynamically linked via a database or image meta-data. Once the current study 22 is closed and committed to the medical record, the study becomes a prior study 24 and typically can no longer be edited or modified.

The system 2 includes a proximity module which given an image slice in a study such as displayed by the radiology viewport 4, returns a set of proximate annotations which include annotations in a range of adjacent image slices and a measure of the closeness of each proximate annotation to the given image slice. The range of adjacent image slices is called the depth. The depth includes a system default and can include a user preference, and be dynamically modified. For example, with a default depth can be set at ±10 images and the current image slice is 87 of 200 images slices, the annotations returned will be associated with image slices 77-86 and 88-97 as the proximate annotations to image slice 87. The healthcare practitioner can dynamically modify the depth such as by holding the CTRL button and using the mouse wheel to increase the depth to 20 which then returns annotations associated with image slices 67-86 and 88-107 or decrease the depth to 5 which returns the annotations associated with 82-86 and 88-92.

A visualization module 28 included in the system 2, visualizes the returned set of proximate annotations and the measure of closeness associated with each proximate annotation in a clear and intuitive manner. The visualization modules visualizes for display each proximate annotation in reference to the current or selected slice and uses the measure of closeness to visualize each proximate annotation relative to the current or selected slice. The visualization can include visual indicators, audible indicators, combinations, and the like. Visual indicators can include geometric objects, icons, text, combinations and the like. Audible indicators can include sounds and/or tones, variable frequencies, durations, and/or intensities. The visualization can be inline or displayed on the current image or separated from the image slice. For example, the visualization can be separated from the image slice as a pictorial diagram in a corner of the viewport module display. The measure of closeness returned by the proximity module 26 provides for visualization of nearness/farness to the current image slice. The visualization provided by the visualization module is displayed by the radiology viewport module in the display.

A proximity edit module 30 of the system 2 changes the association of a proximate annotation from a proximate image slice to the current image slice. The change effectively moves the annotation to the current image slice and permits the healthcare practitioner to edit the annotation via the annotations module.

The system 2 includes a context extraction module 32 and a matching module 34. These modules extend the concept of proximate annotations to inter-study navigation. A healthcare practitioner compares images between studies to identify changes such as lesion growth and/or necrosis. Annotations provide information about a point in time for a specific image slice. Thus, a healthcare practitioner compares image slices between comparable studies. The context extraction module 32 extracts contextual information from prior patient studies and/or the current study, and the matching module 34 compares the context information for comparability.

Contextual information includes the modality and the body part. The context extraction module 32 extracts information from the data or meta-data associated with key images of prior studies, directory information, current image meta-data, scanner operating parameters, etc. In one embodiment, all contextual information including annotations are stored and associated with key images such as in the DICOM header. Segmental algorithms applied to an image identify organs, anatomical landmarks, segmented structures, etc., which are included in the stored DICOM header.

The matching module 34 determines the comparability of one or more studies. For example, similar modalities such as two MR studies which involve legs can be compared if they are both of the same leg. In another example, a whole body MR and a leg MR may be comparable depending upon other contextual information. The default of comparison includes comparability with the current study. Comparability can be based on best practices, site preferences, and/or individual preferences. If the current study is the whole body and the region of interest indicated by a display image slice shows the chest and a prior study includes only the head, then the three images are not mutually comparable. Modalities can be comparable depending upon the contextual such as thickness, orientation, location, etc. If they are registered which includes anatomical landmarks or segmented structures, comparability is facilitated. Non-comparable studies return a message to the healthcare practitioner. Contextual information can include protocol information such as whether a contrast is applied or not, whether the study is lateral, bilateral, left, or right, etc. Protocol information can include in the case of modality specific information such as MR, the acquisition type (2D/3D), imaging sequence (T1/T2), imaging parameters, and the like.

The matching module 34 determines a corresponding image slice or image in a comparable study. The determination is based on a computed corresponding spatial location. For example, if the selected image slice corresponds to slice 240 of a total of 720 slices in the study, and the patient position determined to be the same, then the matching module returns the image slice in the comparable study which is slice 240. More commonly, the studies have different start and/or stop locations and may have different slice thicknesses. In another example, common locations are determined in both studies and the number of slices between the start and stop locations in each study is determined. If the current study has 900 slices and the selected slices is 300 slices below the starting location and the prior study has 600 slices between the start and stop locations, then the corresponding slice is determined based on the ratio. That is, the corresponding slice in the prior study is $(300/900) \times 600 = 200$, i.e., the $200^{th}$ slice below the common starting location. In another embodiment, the matching module 34 uses multi-modal image registration methods to determine the body part irrespective of the modality. For example, the corresponding start and stop locations would be the slices at the top and bottom of the heart. The information used by the matching module includes information meta-data associated with the image slices and/or generated by the different modalities and/or segmentation methods which identify organs, anatomical landmarks, and/or segmented structures.

The radiology viewport module 4 displays the returned corresponding image slice. The selected image slice and the returned corresponding image slice are both displayed for comparison. The radiology viewport module allows the healthcare practitioner to quickly navigate between images based on information observed or highlighted by an annotation and compare one or more prior studies and the current study. For example, the healthcare practitioner views an annotation on a key-image of a prior study comparable with the current study. The healthcare practitioner right-clicks and selects an option to move to a corresponding image in the current study. Once the radiology viewport displays the image slice from the current study, the healthcare practitioner can scroll or traverse nearby images to identify a suitable slice to annotate. In an another embodiment, the radiology viewport module displays a range of image slices corresponding to the body part based on a selected key image of a prior study and displays a selection dialog which lets the user select the specific slice. This is particularly useful when the range of the target study is large and there are many image slices corresponding to the same general body part, e.g., top versus the bottom of the aorta.

The various modules 4, 20, 26, 28, 30, 32, 34 are suitably embodied by an electronic data processing device, such as the electronic processor or electronic processing device 12 of the workstation 8, or by a network-based server computer operatively connected with the workstation 8 by the network 10, or so forth. The radiology viewport module 4 is suitably embodied by the workstation 8. Moreover, the disclosed navigation and annotation techniques are suitably implemented as a non-transitory storage medium storing instructions (e.g., software) readable by an electronic data processing device and executable by the electronic data processing device to perform the disclosed segmentation and tissue identification techniques.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer-readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Figure 2:
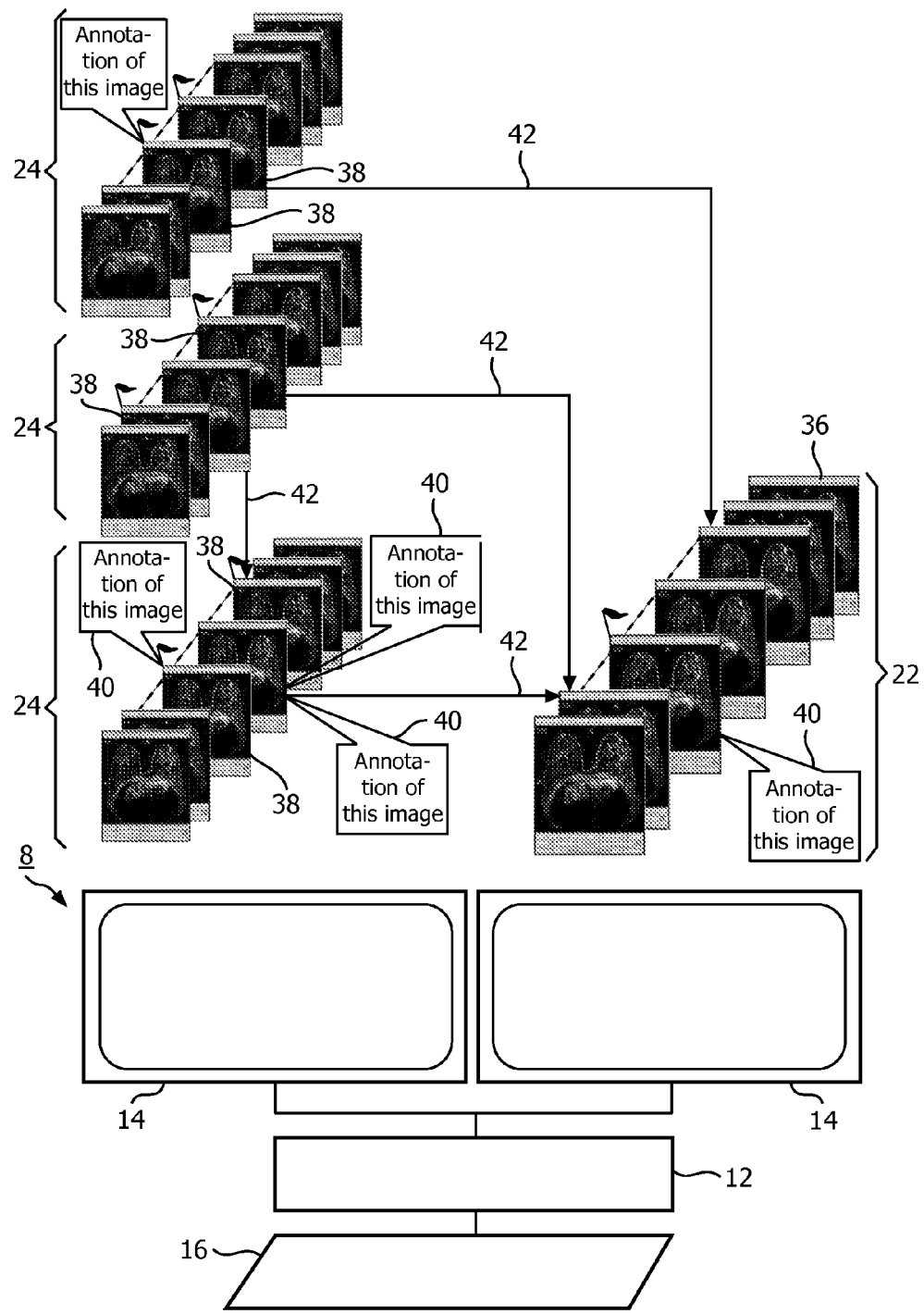

FIG. 2 diagrammatically illustrates an embodiment of multi-study image navigation. Through the radiology viewport module 4 on a display device 14, the healthcare practitioner selects two studies to compare. The contextual information is extracted by the content extraction module 32, and comparability between studies is determined by the matching module 34. The current study 22 includes either a study which is editable and active or a prior study which is not editable. The current study 22 is compared with one or more prior studies 24. Each study includes a plurality of images or image slices 36. A study can include any number of key images 38. An image slice can include any number of annotations 40. Navigation within a study can be linear or include jumps such as jump to a selected slice, such as the 127$^{th}$ slice, entered via the input device 16. Navigation within a study includes proximate annotations.

An example of navigation includes a selection of a key image in prior study. The proximate annotations are displayed which allows the healthcare practitioner to quickly locate, view annotations and select an image slice highlighted by an annotation such as a lesion measurement to compare. The healthcare practitioner is aware of other nearby annotations which may provide better border examples of the lesion. The healthcare practitioner right-clicks the mouse and selects show comparable image in current study. The matching module 34 returns a comparable image slice 42 in the current study 22 based on the slice thickness, the number of image slices, the patient position, etc. The comparable image slice is displayed alongside the selected key image slice by the radiology viewport module 4. The healthcare practitioner can scroll backwards/forwards to determine the best image to make a measurement of the lesion annotated in the selected key image. If the current study is editable, the healthcare practitioner annotates the current study for the lesion size using the annotations module 20. The healthcare practitioner may observe that the border is well defined and also enter an annotation highlighting the well-defined border. If the healthcare practitioner finds a better example navigating the nearby annotations in the prior study which annotated a well-defined border, then the annotation can be moved using the proximity edit module 30. The healthcare practitioner is also aware of any proximate annotations already entered or present in the current study. The edit module also permits connotations to be copied from an earlier image onto an image of the current study and, optionally, modified. For example, segmentation or edge of an earlier image of a lesion can be copied onto the corresponding image to illustrate a change in size or shape.

Figure 3:
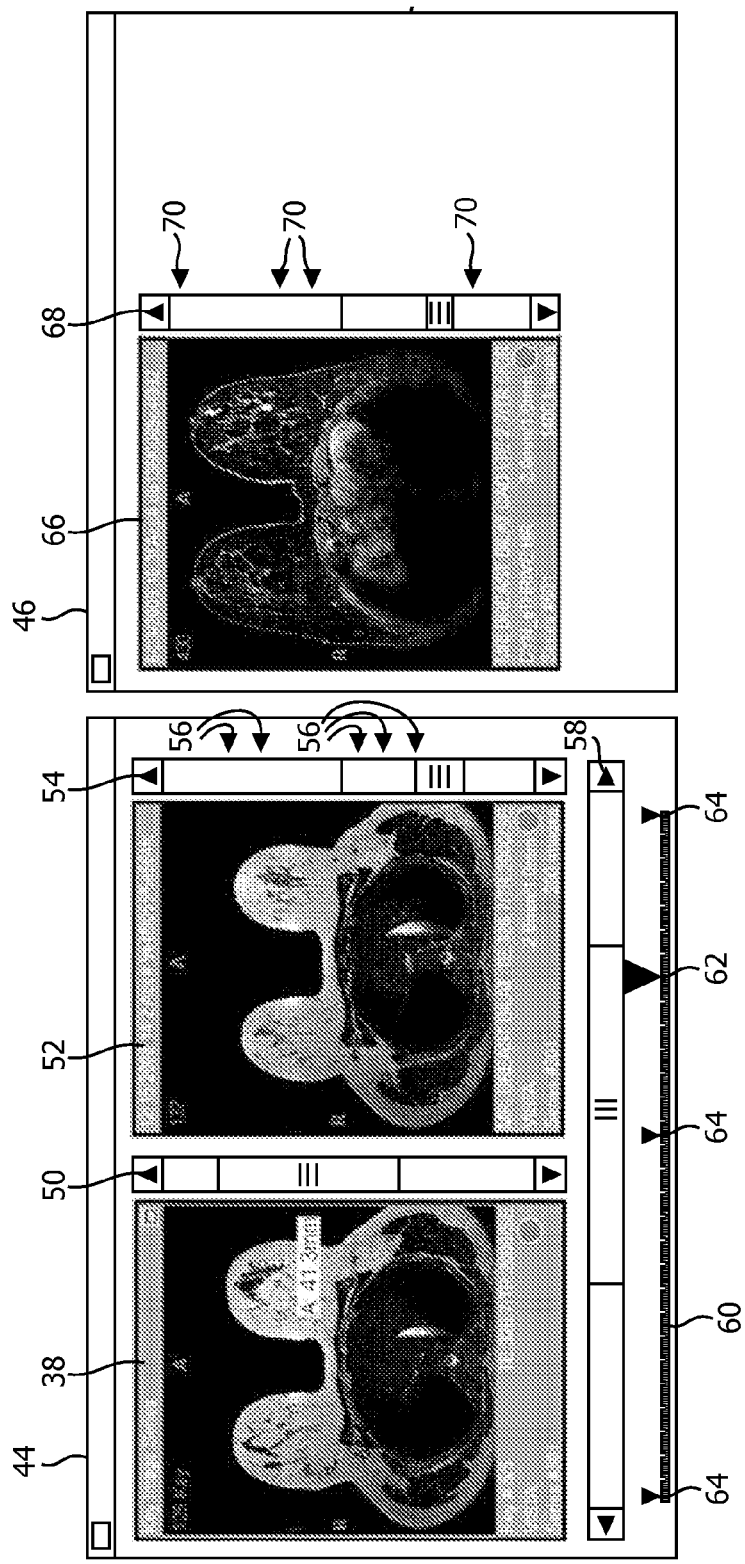
FIG. 3 illustrates an exemplary display of an embodiment of the multi-study image navigation.

FIG. 3 illustrates an exemplary display of an embodiment of the multi-study image navigation. A window display 44 on the left displayed by the radiology viewport module 4 on a display device 14 shows images and navigation information of the comparable prior study 24. A window display 46 on the right displayed by the radiology viewport module 4 on a display device 14 shows images and navigation information of the current study 22.

The navigation information of the prior study includes one or more key images 38. The display of the key image includes a scroll bar 48 to move through the key images, and additional information such as the key image identity 50 which informs the healthcare practitioner as to the current key image identity and number of key images in the study. A second image display in the left window displays a current prior study image 52 based on the key image selected and/or scrolling using a scroll bar 54 by the healthcare practitioner using the input device 16. The display also includes visual indicators 56 of proximate annotations in the prior study. An additional optional scroll-bar 58 is provided via the radiology viewport module which facilitates selecting and moving between multiple comparable prior studies. The line below is represented by a timeline of comparable studies 60 scaled to time. The active prior study displayed in the display is highlighted by a larger visual indicator 62 among several other indicators of comparable prior studies 64.

The navigation of the current study includes a current image 66 and a scroll-bar 68 which through the radiology viewport module 4 and the input device 16 allows the healthcare practitioner to scroll through the images. Proximate annotations are shown in the scroll-bar by visual indicators 70.

Figure 4A:
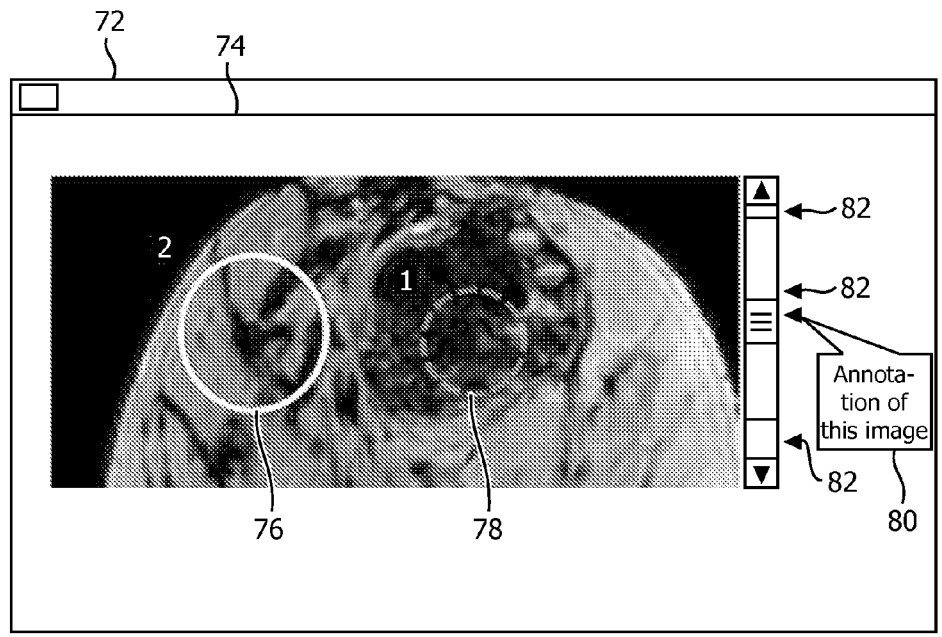
FIG. 4A and FIG. 4B illustrates an exemplary display of proximate annotations.
Figure 4B:
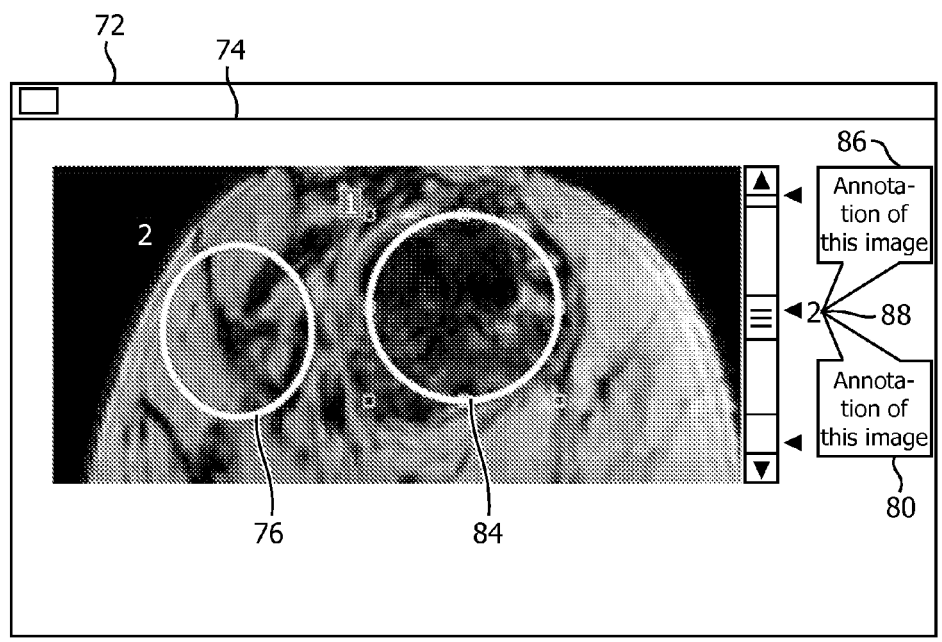

FIG. 4A and FIG. 4B illustrates an exemplary display of proximate annotations. With reference to FIG. 4A, a display 72 by the radiology viewport module 4 shows a display of a current selected image 74 which includes both an inline display of an annotation 76 and an inline display of a proximate annotation 78, and a separate or sidebar displays of an annotation 80 and visual indicators of proximate annotations 82. The inline display of the annotation 76 includes a circular geometric shape with a solid line outline. The sidebar display of the annotation 80 includes a text box. In the instance of a voice annotation, the text box can be an icon which when selected plays the voice annotation through the speaker 18 of FIG. 1. The inline proximate annotation 78 includes a sized circular geometric shape with a slightly transparent outline (shown in dashes) visualized by the visualization module 28. The size, transparency, and dotted line indicate a proximate annotation different from the annotation 80.

With reference to FIG. 4B, the display 72 displays the same selected image, but the proximate annotation 78 of FIG. 4A has been selected and the association changed by the proximity edit module 30 to the current image slice 74. The prior proximate annotation 80 is now a second annotation 84 to the current image slice 74. The second annotation text 86 is added to the sidebar display, and a number is added to the visual indicator 88 that 2 annotations are now associated with the current image slice.

Figure 5A:
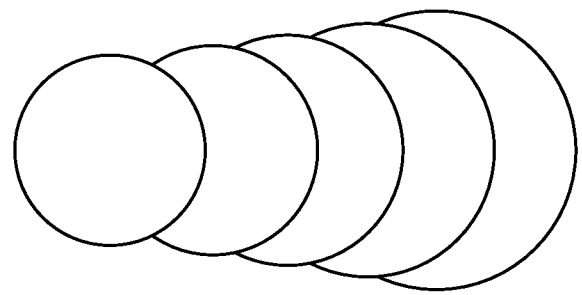
FIG. 5A-5C illustrates exemplary embodiments of visualization of proximate geometric annotations.
Figure 5B:
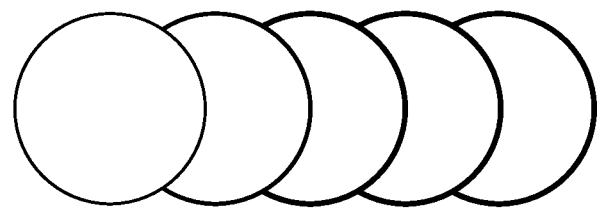
Figure 5C:
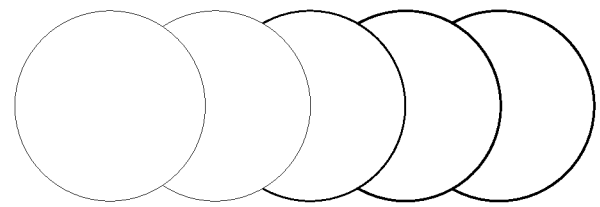

FIG. 5A-5C illustrates exemplary embodiments of visualization of proximate geometric annotations. The visualization module 28 visualizes the proximate annotations in the current or selected image. With reference to FIG. 5A, the proximate annotation can be represented as scaled objects such as circles of different diameter. For example, the largest scale is how the annotation is visualized when displayed as the annotation associated with the current slice, and consecutively smaller in scale the further the annotation is away from the current image slice as a proximity annotation. The scale is based on the measure of closeness returned by the proximity module 26.

With reference to FIG. 5B, nearness/farness can be visualized by transparency. Using the same objects in reference to FIG. 5A, distance can also be indicated by transparency, such as the transparency of the geometric circular outline. That is, the selected number of slices in advance (depth), the annotation appears faintly. As the radiologist navigates toward the annotated images, the annotation becomes progressively less transparent. After passing the annotated image, the annotation progressively fades. With reference to FIG. 5C, nearness/farness can be visualized by other visual indicators such as consistency of an outline. For example, a dotted outline of a geometric object can be with the dots farther away from each other the further the distance away and with the dots closer together or elongated into longer line segments the closer the distance until a solid line is formed as an annotation in the current slice.

With the various techniques to indicate distance, forward and reverse directions can be indicated. For example, scale of an object can indicate absolute distance of measure of closeness while transparency can indicate forward distance and consistency of an outline can indicate backward distance. Forward/backward can also be denoted by color. The visualization in another embodiment can be user defined. Direction can also be inherent in the change in visualization from image to image as the proximate visualization changes. For example, as the healthcare practitioner moves toward a proximate annotation the scale increases and when moving past the scale decreases. The change in scale which is increase/decreasing provides the healthcare practitioner with a sense of direction of the proximate annotation.

FIG. 6 flowcharts one method of multi-study image navigation. In a step 90, a comparable image study is identified based on extracted contextual information. Contextual information is extracted from the current study and a prior study by the context extraction module 34. The contextual information includes the modality, the body part, starting and ending formats of the study, slice thickness, and the like. The contextual information can include the protocol information. The contextual information can include information stored in meta-data such as the DICOM header. The contextual information can be extracted from key images previously identified in the study.

An image of the prior study is selected in a step 92. The selected image can include an identified key image. The image is selected using the radiology viewport module 4 and the at least one input device 16.

The matching module 34 based on the contextual information and the selected image returns a corresponding image or image slice in the current study in a step 94. The radiology viewport module displays in a step 96 the display which includes the selected image and the corresponding or comparable image returned by the matching module. Optionally, the radiologist scrolls a few images either way to assure the less matched image is selected. In a decision step 98, the healthcare practitioner via the radiology viewport module and at least one input device can indicate another selected image and/or navigate to adjacent images of the returned image. Optionally, using the edit module the radiologist can annotate the selected corresponding image which may include copying parts of the prior annotation. If the healthcare practitioner indicates a decision to select another image, such as by a mouse, pull down menu, dialog box, etc., then the method returns to the earlier step 92 of selecting an image.

In another embodiment, the healthcare practitioner can indicate a decision 100 for a different comparable study such as by a mouse movement of a timeline scroll bar, pull down menu, or dialog box. A decision to select a different study returns the healthcare practitioner to an earlier step 90 of selecting a comparable study.

FIG. 7 flowcharts one method of visualizing proximate annotations. In a step 102, the depth or number of adjacent images slices is computed or assigned. The depth can include a system default, user preference, or be dynamically changed by the system or healthcare practitioner such as with pressing the CTRL button of the keyboard and the scrolling with the wheel of the mouse.

The proximate annotations are identified in relationship to the current image and the depth in a step 104. The proximate annotations are identified by the proximity module 26. The proximate annotations include the annotations of the adjacent images included in the range indicated by the depth. The visualization module 28 visualizes the proximate annotations in a step 106. The proximate annotations can be visualized as inline and/or sidebar. The proximate annotations can include representations of the annotation such as geometric objects, icons, other visual indicators, audible indicators and the like. The proximate annotations can be visualized by scale, transparency, and consistency, color, etc. For example, the annotation became more prominent with greater proximity.

The proximate annotations, annotations, images and user interface objects such as menus, panels, scroll-bars, etc. are displayed in a step 108. The display is managed by the radiology viewport module 4 and displayed on one or more display devices 14.

In a decision step 110, the healthcare practitioner can indicate an image change such as by scrolling to a different image or a right-click with a jump to different image. By changing images the method returns to an earlier step 104. In a second decision step 112, a change in depth can be indicated such as by input from the input devices 16. The decision to change the depth returns to an earlier step 102.

FIG. 8 flowcharts one method of editing proximate annotations. In a step 114, the proximate annotation is selected. The proximate annotation is selected by the radiology viewport module 4, which returns the proximate annotation selected to the proximity edit module 30. For example, a mouse cursor and click can be used to identify to select a visualized proximate annotation. In a step 116, the association of the proximate annotation is changed or moved from the adjacent image slice associated with the proximate annotation to the current slice. The change or move can be confirmed by a dialog box, etc. The change in association is made by the proximity edit module 30. The annotation which is now present in the current image slice can be edited by the annotations module 20 as an annotation of the current image slice.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A medical image navigation system, comprising:
at least one processor programmed to:
navigate a plurality of image slices of a study and based on input from at least one input device select at least one image which is displayed and any annotations associated with the selected at least one image on a display device, and further navigate at least one prior study which includes a plurality of images and at least one key image;
return at least one proximate annotation for the selected image slice;
visualize the at least one proximate annotation for the returned at least one proximate annotation which is displayed on the selected at least one image;
extract and associate contextual information with the at least one key image and the selected at least one image, and the contextual information includes a modality and a body part,
compare the contextual information to determine if the studies are comparable,
return a location of an image slice in the study corresponding to the at least one key image of the at least one prior study; and
move and/or copy the association of the at least one proximate annotation from the key image to the selected image slice.

2. The system according to claim 1, wherein the at least one proximate annotation is located in a selected number of adjacent slices.

3. The system according to claim 2, wherein the selected number of adjacent slices is determined by at least one of:
a fixed number present in the system;
a fixed number according to the user of the system; and
a number dynamically adjusted by at least one input device.

4. The system according to claim 1, wherein the at least one processor is further programmed to visualize the at least one proximate annotation by at least one of:
a visual indicator of a geometric representation of the at least one proximate annotation which includes a dashed line outlining the geometric representation becoming more solid the nearer the slice with the at least one proximate annotation;
a visual indicator which includes a geometric representation of the at least one proximate annotation which becomes less transparent the nearer the slice with the at least one proximate annotation;
a visual indicator which includes a scaled geometric representation of the at least one proximate annotation which becomes larger the nearer the slice with the at least one proximate annotation.

5. The system according to claim 1, wherein the at least one processor is further programmed to visualize the at least one proximate annotation by at least one of:
a visual indicator located on a scroll bar which is scaled to indicate the proximity of the at least one proximate annotation;

an audible indicator sounded by an output device which sounds louder the nearer the at least one proximate annotation;

an audible indicator sounded by an output device which indicates the proximity of the at least one proximate annotation; and a visual indicator which includes a pictorial diagram located in the display and separate from the selected image.

6. The system according to claim 1, wherein the at least one processor is further programmed to select at least one image slice for which a comparison of the contextual information is performed;

wherein the selected at least one image slice is displayed on the display.

7. The system according to claim 6, wherein the contextual information includes at least one of:

an application of a contrast agent;

a study scope which includes lateral, bilateral, left, and right views; and for magnetic resonance modality, an acquisition type which includes 2D and 3D;

for magnetic resonance modality, an imaging sequence.

8. The system according to claim 7, wherein the location returned is based on the image slice thickness and a number of images slices in each compared study and selected corresponding start and end slices.

9. The system according to claim 8, wherein the location returned is based on a multi-modality image registration and in the at least one key image at least one of:

a segmented structure; and an identified anatomical landmark.

10. The system according to claim 9, further including at least one of:

a picture archiving and communication system (PACS); and a radiology information system (RIS).

11. A method of navigating medical images, comprising:

with a computer, identifying at least one annotation associated with an image slice within a selected number of adjacent image slices of a plurality of image slices to a selected image slice;

with the computer, visualizing the identified annotations; and displaying the selected image slice and visualized annotations on a display device;

with the computer, identifying a comparable prior study which includes a plurality of images based on an extracted context of the comparable prior study and an extracted context of the selected image slice study;

with the computer, selecting one of the plurality of images of the comparable study;

with the computer, matching the selected one image location of the comparable study to a corresponding image slice of the plurality of image slices; and with a monitor, displaying the selected one image and the corresponding image slice.

12. A non-transitory computer-readable storage medium carrying software which controls one or more electronic data processing devices to perform the method according to claim 11.

13. An electronic data processing device configured to perform the method according to claim 11.

14. A medical image navigation system, comprising:

at least one processor programmed to:

navigate a plurality of image slices of a current study and at least one prior study which includes a plurality of images and at least one key image, and based on input from at least one input device select at least one key image, which is displayed on a display device with an associated image slice in the current study;

extract and associate contextual information with the at least one key image and the current study;

compare the contextual information to determine if the studies are comparable, and return a corresponding image slice in the current study corresponding to a selected at least one key image of the at least one prior study.

15. The method according to claim 11, wherein the at least one processor is further programmed to at least one of move and copy the association of the at least one proximate annotation from the key image to the selected image slice.

16. The method according to claim 11, further including:

selecting at least one image slice for which a comparison of the contextual information is performed; and displaying the selected at least or age slice on the display.

17. The system according to claim 14, wherein the at least one processor is further programmed to at least one of move and copy the association of the at least one proximate annotation from the key image to the selected image slice.

18. The system according to claim 17, further including a display, and wherein the at least one processor is further programmed to:

return at least one proximate annotation for the selected image slice;

visualize the at least one proximate annotation for the returned at least one proximate annotation which is displayed on the selected at least one image;

return a location of an image slice in the study corresponding to the at least one key image of the at least one prior study based on the comparison of the contextual information of the at least one current study and the at least one prior study.

19. The system according to claim 18, wherein the at least one processor is further programmed to select at least one image slice for which a comparison of the contextual information is performed;

wherein the selected at least one image slice is displayed on the display.

20. The system according to claim 14, wherein the at least one processor is further programmed to visualize the at least one proximate annotation by at least one of:

an audible indicator sounded by an output device which sounds louder the nearer the at least one proximate annotation;

an audible indicator sounded by an output device which indicates the proximity of the at least one proximate annotation; and a visual indicator which includes a pictorial diagram located in the display and separate from the selected image.

* * * * *